United States Patent
Lamminmaki et al.

(10) Patent No.: US 11,540,755 B2
(45) Date of Patent: Jan. 3, 2023

(54) SYSTEMS AND METHODS FOR LOW POWER PULSE OXIMETRY

(71) Applicant: GE Precision Healthcare LLC, Milwaukee, WI (US)

(72) Inventors: Sakari Matias Lamminmaki, Espoo (FI); Kari Piipponen, Kerava (FI)

(73) Assignee: GE Precision Healthcare LLC, Milwaukee, WI (US)

( * ) Notice: Subject to any disclaimer, the term of this patent is extended or adjusted under 35 U.S.C. 154(b) by 187 days.

(21) Appl. No.: 17/143,020

(22) Filed: Jan. 6, 2021

(65) Prior Publication Data
US 2021/0121109 A1   Apr. 29, 2021

Related U.S. Application Data

(63) Continuation of application No. 16/180,847, filed on Nov. 5, 2018, now Pat. No. 10,912,505.

(51) Int. Cl.
   A61B 5/1455   (2006.01)
   H05B 45/37   (2020.01)
   A61B 5/024   (2006.01)

(52) U.S. Cl.
   CPC ......... *A61B 5/14552* (2013.01); *H05B 45/37* (2020.01); *A61B 5/02433* (2013.01); *A61B 2560/0209* (2013.01); *A61B 2562/0238* (2013.01)

(58) Field of Classification Search
   CPC .............. A61B 5/1455; A61B 5/14551; A61B 2560/0204; A61B 2560/0209; H05B 33/0815
   See application file for complete search history.

(56) References Cited

U.S. PATENT DOCUMENTS

| | | |
|---|---|---|
| 5,675,490 A | 10/1997 | Bachhuber |
| 5,697,374 A | 12/1997 | Odagiri et al. |
| 6,697,655 B2 | 2/2004 | Sueppel et al. |
| 6,697,658 B2 | 2/2004 | Al-Ali |
| 6,862,652 B1 | 3/2005 | Tsuji |
| 6,912,413 B2 | 6/2005 | Rantala et al. |
| 7,162,288 B2 | 1/2007 | Nordstrom et al. |
| 7,295,866 B2 | 11/2007 | Al-Ali |
| 7,382,247 B2 | 6/2008 | Welch et al. |
| 7,499,740 B2 | 3/2009 | Nordstrom et al. |
| 8,457,703 B2 | 6/2013 | Al-Ali |
| 8,515,509 B2 | 8/2013 | Bruinsma et al. |
| 8,571,622 B2 | 10/2013 | Huiku et al. |
| 9,237,855 B2 | 1/2016 | Hong et al. |
| 2005/0187446 A1 | 8/2005 | Nordstrom et al. |
| 2012/0146531 A1 | 6/2012 | Uchimoto et al. |

(Continued)

FOREIGN PATENT DOCUMENTS

| | | |
|---|---|---|
| EP | 2832289 A1 | 2/2015 |
| WO | 2005082240 A1 | 9/2005 |
| WO | 2005089640 A2 | 9/2005 |

*Primary Examiner* — Eric F Winakur
(74) *Attorney, Agent, or Firm* — McCoy Russell LLP

(57) ABSTRACT

Methods and systems are provided for a light-emitting diode (LED) drive circuit of an optical probe. As an example, a method for an optical probe including an LED in an LED drive circuit comprises reducing power consumption of the LED drive circuit by adjusting a drive voltage of the LED drive circuit based on one or more LED drive circuit characteristics and one or more LED drive circuit operating parameters. In this way, the LED drive circuit may be efficiently operated.

19 Claims, 5 Drawing Sheets

(56) References Cited

U.S. PATENT DOCUMENTS

| | | |
|---|---|---|
| 2013/0267804 A1 | 10/2013 | Al-Ali |
| 2014/0213912 A1 | 7/2014 | Su |
| 2015/0190078 A1 | 7/2015 | Lisogurski |
| 2015/0196239 A1 | 7/2015 | Meehan et al. |
| 2015/0199485 A1 | 7/2015 | Borges |
| 2015/0289791 A1 | 10/2015 | Marcus |
| 2018/0235525 A1 | 8/2018 | Blanken |
| 2018/0353111 A1 | 12/2018 | Buxton et al. |

SYSTEMS AND METHODS FOR LOW POWER PULSE OXIMETRY

CROSS-REFERENCE TO RELATED APPLICATION

This application is a continuation of U.S. patent application Ser. No. 16/180,847, filed on Nov. 5, 2018, entitled "SYSTEMS AND METHODS FOR LOW POWER PULSE OXIMETERY." The entire contents of the above-referenced application is hereby incorporated by reference for all purposes.

FIELD

Embodiments of the subject matter disclosed herein relate to biological probes, sensors, and methods, and in particular, to photoplethysmography probes and methods.

BACKGROUND

Photoplethysmography (PPG) relates to the use of optical signals transmitted through or reflected by blood-perfused tissues for monitoring a physiological parameter of a subject (also referred to as a patient herein). In this technique, one or more emitters are used to direct light at a tissue, and one or more detectors are used to detect the light that is transmitted through or reflected by the tissue. The volume of blood of the tissue affects the amount of light that is transmitted or reflected, which is output as a PPG signal. As the blood volume in a tissue changes with each heartbeat, the PPG signal also varies with each heartbeat.

Pulse oximetry is, at present, the standard of care for continuously monitoring arterial oxygen saturation ($SpO_2$). Pulse oximeters include PPG probes that use red (~660 nm) and infrared (~940 nm) light to determine physiological parameters (e.g., blood characteristics) of the subject, including $SpO_2$, pulse rate, and pulsating blood flow (e.g., blood perfusion) at the site of measurement. Conventional pulse oximetry probes are typically mounted to an extremity of the subject (e.g., a finger or ear lobe).

BRIEF DESCRIPTION

In one embodiment, a method for a pulse oximeter probe including a light emitting diode (LED) includes reducing power consumption of an LED drive circuit by adjusting drive voltage of the LED drive circuit based on one or more LED drive circuit characteristics and one or more LED drive circuit operating parameters.

Thus, the drive voltage of the LED drive circuit may be adjusted dynamically based on voltage losses of the LED drive circuit, which may include voltage losses measured during manufacture of the probe as well as voltage losses measured or calculated dynamically during use of the probe (e.g., when the probe is measuring SpO2, pulse rate, and/or perfusion of a patient). Further, the drive voltage may be adjusted based on LED drive operating parameters when the probe is used to measure patient physiological parameters, which may include LED current, pulse length, and current regulator reference voltage. By measuring or estimating the actual voltage losses, which may vary among probes and change as probe operation changes (e.g., as patient tissue changes), a drive voltage may be output from a voltage regulator of the drive circuit that better matches the voltage losses and demands of the LED drive circuit, thereby lowering overall power consumption of the probe.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
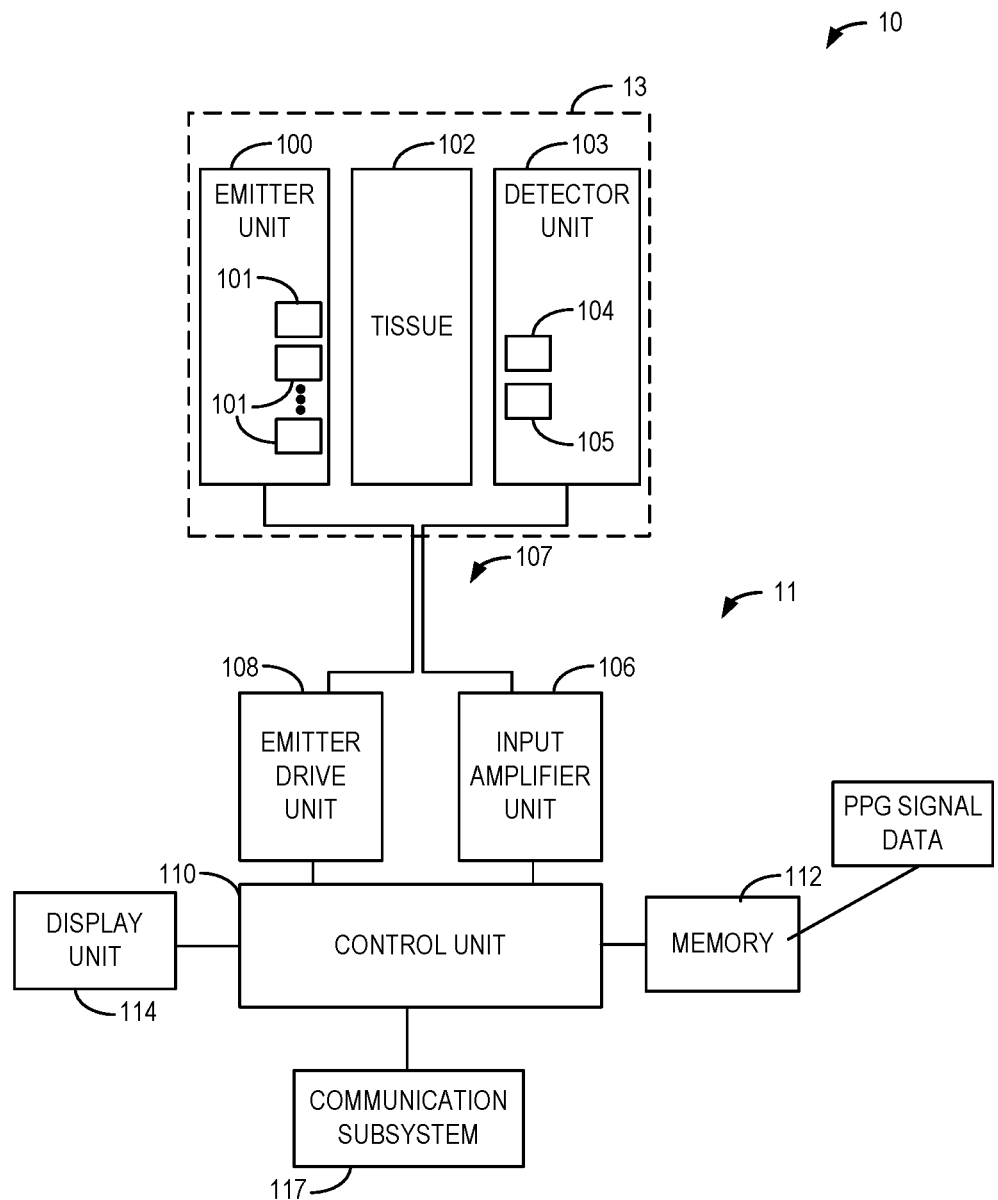
FIG. 1 is a block diagram illustrating an example pulse oximetry system.

The following description relates to various embodiments of an optical probe. The probe may be included in a pulse oximetry sensor or system, such as the system of FIG. 1, for determining physiological parameters of a patient. The optical probe may include two light emitters, herein light emitting diodes (LEDs), driven by a drive circuit, such as the drive circuit illustrated in FIG. 2. Characteristics of the LED drive circuit affecting the voltage losses may be determined at the time of manufacture and during use of the optical probe. LED drive circuit voltage losses, and thus desired LED voltage, may be estimated based on LED drive circuit characteristics and operating parameters in order to dynamically optimize LED drive voltage, as shown by the method of FIGS. 3A and 3B. By dynamically optimizing LED drive voltage, the LED drive voltage may be lowered, thereby lowering power consumption of the pulse oximetry system. Further, a low loss switching voltage regulator may be used to provide the LED drive voltage. To reduce interference, the switching voltage regulator may be turned off during LED pulses, as shown by the timing diagram of FIG. 4.

A pulse oximeter comprises a computerized measuring unit and a probe attached to a patient, typically a finger or ear lobe of the patient. The probe includes a light source for sending an optical signal through tissue of the patient and a photo detector for receiving the signal transmitted through or reflected from the tissue. On the basis of the transmitted and received signals, light absorption by the tissue may be determined. During each cardiac cycle, light absorption by the tissue varies cyclically. During the diastolic phase, absorption is caused by venous blood, non-pulsating arterial blood, cells and fluids in tissue, bone, and pigments. The level of light transmitted at end of the diastolic phase is typically referred to as the "DC component" of the total light transmission. During the systolic phase, there is an increase in light absorption (e.g., a decrease in transmitted light) compared with the diastolic phase due to the inflow of arterial blood into the tissue on which the pulse oximetry probe is attached. A crucial pulse oximetry principle is how the measurement can be focused on the blood volume representing the arterial blood only. In pulse oximetry, this is done by taking the pulsating arterial blood portion (the "AC signal") from the total transmission signal and normalizing this signal by the "DC" component. The resulting "AC/DC" signal is called the PPG waveform. Pulse oximetry is thus based on the assumption that the pulsatile component of the absorbance is due to arterial blood only.

In pulse oximetry, arterial blood is typically modeled as containing two species of hemoglobin: oxyhemoglobin ($HbO_2$) and reduced hemoglobin (Hb). Oxyhemoglobin is hemoglobin that is fully saturated with oxygen, and reduced hemoglobin is without oxygen. Arterial oxygen saturation measured by pulse oximetry ($SpO_2$) is defined as the percentage of $HbO_2$ divided by the total amount of hemoglobin ($HbO_2$+Hb). In order to distinguish between the two species of hemoglobin, light absorption is measured at two different wavelengths. The probe of a traditional pulse oximeter includes two different light sources, such as light-emitting diodes (LEDs) or lasers, that emit light at two different wavelengths. The wavelength values widely used are 660 nm (red light) and 900 nm (infrared light), as the two species of hemoglobin have substantially different absorption at these wavelengths. Each light source is illuminated in turn at a frequency that is typically several hundred Hz.

Pulse oximeter probes may be used in a variety of medical contexts, including continuous patient monitoring. During continuous patient monitoring, output from a pulse oximeter probe may be collected and/or displayed at a specified rate over a relatively long duration. The duration of the continuous patient monitoring may vary, but in some contexts the monitoring may occur for multiple hours or longer. Thus, it may be desirable to configure the pulse oximeter as a remote sensor that communicates wirelessly with a central unit, thereby allowing a patient undergoing monitoring to be untethered from wired connections and associated bulky componentry. However, pulse oximeter probes may demand a relatively high amount of power in order to drive the LEDs at the above-described wavelengths and frequencies, thus limiting the ability to configure the probes as remote sensors. For example, batteries that are small and/or inexpensive enough for use in a remote pulse oximeter sensor may not store sufficient charge to power the pulse oximeter for an extended amount of time. Further, even in wired systems where ample charge may be available, power consumption in the pulse oximeter may be higher than necessary, leading to wasted energy use, higher heat dissipation, or other issues.

Pulse oximeter probe LED drive power consumption has a key role in a low power pulse oximetry power budget. LED average power consumption is proportional to LED average current and LED drive voltage. In conventional pulse oximetry, a constant predetermined LED drive voltage is used based on a worst case scenario of the estimated voltage losses (also referred to as a voltage drop) in the LED drive circuit. Thus, in many cases, the LED drive voltage is higher than necessary, leading to higher than needed power consumption.

For example, the LED drive voltage is configured to be higher than the voltage losses in the LED drive circuit. Voltage loss in the LED drive circuit may be attributed to a voltage drop in a voltage regulator and a bulk capacitor, probe cable and connector resistances, a voltage drop over the LEDs, a voltage drop over the current regulator, and a possible H-bridge voltage drop. In conventional pulse oximetry, the worst case scenario for each of the voltage losses in the LED drive circuit is estimated, and the LED drive voltage is hard coded based on that analysis.

Thus, according to embodiments of the disclosure presented herein, LED drive voltage may be optimized based on probe manufacturing data written in permanent memory and/or based on dynamically determined operating parameters and measured variables. By optimizing the drive voltage in a dynamic manner, power consumption by the pulse oximeter may be reduced, thereby extending battery life and enabling the configuration of the pulse oximeter as a remote sensor.

In an example, the drive voltage may be optimized based on the voltage drop in the voltage regulator and in the bulk capacitor. Conventional pulse oximeters use a low efficiency linear regulator to create low noise LED drive voltage, which may consume excess power. Thus, a low loss LED drive may be included in the pulse oximeter of the present disclosure that is based on a switching voltage regulator. To reduce interference, the switching regulator may be turned off during an LED pulse, and the bulk capacitor may be used to provide the energy during the LED pulse. The output voltage of the switching regulator may be adjusted with high efficiency to optimize the transmission voltage.

In an example, the drive voltage may be optimized based on the voltage drop in the bulk capacitor. The voltage drop in the bulk capacitor may be calculated based on the LED pulse length, LED current, and capacitance. Thus, the LED pulse length, LED current, and capacitance may be used to dynamically optimize the LED drive voltage.

In an example, the drive voltage may be optimized based on the probe cable and connector resistances and used (e.g., supplied) LED current (LED current may be adjustable, e.g., in range of 10-200 mA). Probe cable and connector resistances may be measured during manufacture of the pulse oximeter and written to permanent memory to optimize LED drive voltage. A pulse oximeter monitor may also measure the cable/connector resistance when the probe is connected and optimize LED drive voltage dynamically.

In an example, the drive voltage may be optimized based on the voltage drop over the LED. The voltage drop over the LED depends on LED emission wavelength, materials, and used forward current. The voltage drop over the LED with different LED currents may be characterized in probe manufacturing. The pulse oximeter may also measure LED anode and cathode voltages to calculate the voltage drop in the LEDs/probe/LED drive. LED drive voltages may be dynamically optimized independently for each individual LED of the pulse oximeter based on the estimated voltage losses.

In an example, the drive voltage may be optimized based on the voltage measured over the LED current regulator. The current regulator may provide accurate and noise free LED current only if the voltage over the current regulator is kept over a minimum voltage specified for the driver, e.g., 0.8 V. If the voltage over the current regulator is higher than the minimum voltage, the extra voltage is converted to heat in the regulator. The voltage may be measured periodically, e.g., once a second, or when LED peak current or duty cycle (LED pulse length or pulse frequency) is changed and LED drive voltages are adjusted accordingly. Voltage drop over the LED depends on LED wavelength, and thus it is favorable to have separate LED drive voltage and LED driver circuits for red and infrared LEDs.

In an example, the drive voltage may be optimized based on an LED current regulator reference voltage and a possible H-bridge. Conventional pulse oximeters use a constant current regulator reference voltage that is based on the worst case analysis of, e.g., a desired signal-to-noise ratio (SNR) and a maximum required LED current. Current regulator voltage loss is dependent on the current regulator reference voltage. The current regulator reference voltage may be adjusted dynamically based on a LED drive target SNR and a required LED current dynamic range. A higher reference voltage provides higher SNR and higher LED drive current. The LED drive target SNR may be set based on a perfusion of tissue being measured by the pulse oximeter probe. For example, when the perfusion (e.g., % modulation) is higher than a threshold, the target SNR may be reduced. The threshold may correspond to a perfusion value above which higher SNRs will not result in more accurate perfusion measurements. The maximum required LED current can be determined based on, e.g., the system SNR target and tissue attenuation. When the LED drive target SNR or current driver maximum LED current is decreased, the current regulator reference voltage and the LED drive voltage can be decreased accordingly. The LED drive voltage also can be optimized dynamically based on the LED scheme (common cathode vs. back to back); the common cathode LED scheme does not require an H-bridge, and thus, the required LED drive voltage is lower.

FIG. 1 is a block diagram of one embodiment of a multi-wavelength pulse oximetry system 10. Light transmitted from an emitter unit 100 passes into patient tissue 102. The emitter unit includes multiple light sources 101, such as light-emitting diodes (LEDs), with each light source having a dedicated wavelength. Each wavelength forms one measurement channel on which PPG waveform data are acquired. The number of sources/wavelengths is at least two.

The light transmitted through the tissue 102 is received by a detector unit 103, which comprises two photo detectors 104 and 105 in this example. For example, photo detector 104 may be a silicon photodiode, and photo detector 105 may be a second silicon photodiode with different spectral characteristics or an indium gallium arsenide (InGaAs) photodiode. The emitter and detector units form a probe subunit 13 of the pulse oximetry system 10. In some examples, the photo detectors may be configured/arranged to receive light which has reflected from the tissue in addition to or alternatively to receiving light that is transmitted through the tissue.

The probe subunit 13 may be coupled to a drive and processing subunit 11 via a cable 107 and one or more connectors. For example, a connector may be present on an end of cable 107 to connect cable 107 and probe subunit 13 to drive and processing subunit 11. In this way, probe subunit 13 may be removably coupled to drive and processing subunit 11. In other examples, probe subunit 13 and drive and processing subunit 11 may be integrated into the same housing.

Drive and processing subunit 11 may include an input amplifier unit 106 and an emitter drive unit 108. The photo detectors convert the optical signals received into electrical pulse trains and feed them to an input amplifier unit 106. The amplified measurement channel signals are further supplied to a control unit 110, which executes instructions stored in memory 112 to convert the signals into digitized format for each wavelength.

The control unit 110 further controls emitter drive unit 108 to alternately activate the light sources. To activate the light sources, the emitter drive unit 108 may include a voltage source, such as a battery, which will be described in more detail below. As mentioned above, each light source is typically illuminated several hundred times per second. With each light source being illuminated at such a high rate compared to the pulse rate of the patient, the control unit 110 obtains a high number of samples at each wavelength for each cardiac cycle of the patient. The value of these samples varies according to the cardiac cycle of the patient, the variation being caused by the arterial blood.

The digitized PPG signal data at each wavelength may be stored in memory 112 of the control unit 110 before being processed further according to non-transitory instructions (e.g., algorithms) executable by the control unit 110 to obtain physiological parameters. Memory 112 may comprise a suitable data storage medium, for example, a permanent storage medium, removable storage medium, and the like. Additionally, memory 112 may be a non-transitory storage medium. In some examples, the system 10 may include a communication subsystem 117 operatively coupled to one or more remote computing devices, such as hospital workstations, smartphones, and the like. The communication subsystem 117 may enable the output from the detector units (e.g., the digitized PPG signal data) to be sent to the one or more remote computing devices for further processing and/or the communication subsystem may enable the output from the algorithms discussed below (e.g., determined physiological parameters) to be sent to the remote computing devices. The communication subsystem 117 may include wired and/or wireless communication devices compatible with one or more different communication protocols. As non-limiting examples, the communication subsystem 117 may be configured for communication via a wireless telephone network, a local- or wide-area network, and/or the Internet.

Algorithms may utilize the same digitized signal data and/or results derived from the algorithms and stored in the memory 112, for example. For example, for the determination of oxygen saturation and pulse transit time (PTT), the control unit 110 is adapted to execute an $SpO_2$ algorithm and a PTT algorithm, respectively, which may also be stored in the memory 112 of the control unit 110. Additional algorithms, such as a blood pressure algorithm, a hypovolemia algorithm, and a respiration rate algorithm, may also be stored in memory 112 for determining blood pressure, an indication of hypovolemia, and respiration rate, respectively. The obtained physiological parameters and waveforms may be shown on a screen of a display unit 114. Further, in some examples, the control unit, memory, and/or other subsystems may be located remotely from the rest of the sensor on a separate device, and the signal data from the detector units may be sent to the separate device for processing.

The input amplifier unit 106, the control unit 110 and memory 112, the emitter drive unit 108, probe subunit 13, and/or additional components (the display unit, for example) may collectively form a sensor. As used herein, the term "probe" may refer to the probe and the attachment parts that attach the optical components of the probe to the tissue site. The term pulse oximeter or sensor may refer to a unit comprising a probe, an analog front end, and a signal processing unit that calculates $SpO_2$ and other blood characteristics. In a multi-parameter body area network system, the system typically represents a set of multiple sensors, e.g., the different physiological parameter measurements. Therefore, the whole measurement system may comprise of several sensors and their associated probes, and the sensors may communicate to a common hub in which the parameters' information is integrated.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 2:
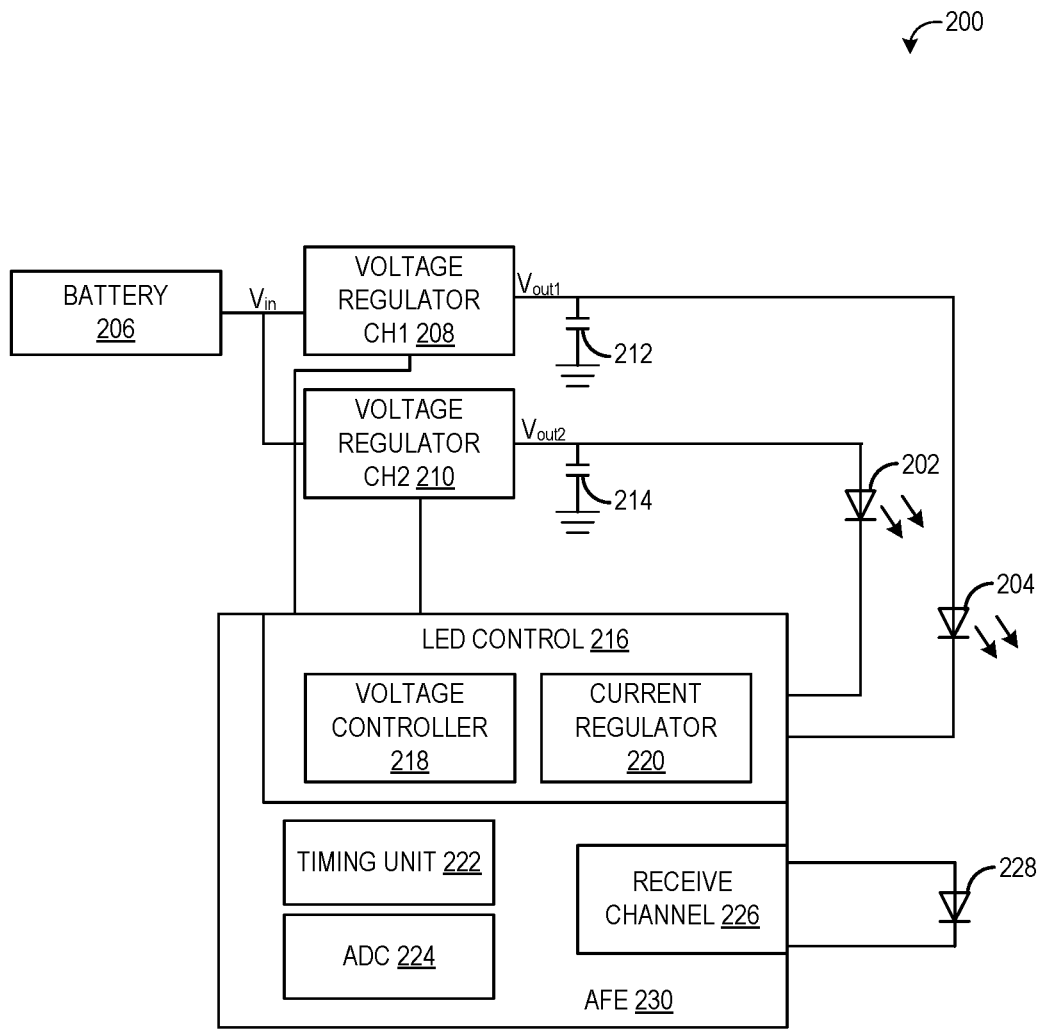
FIG. 2 schematically shows an example LED drive circuit for a pulse oximetry system.
Figure 3A:
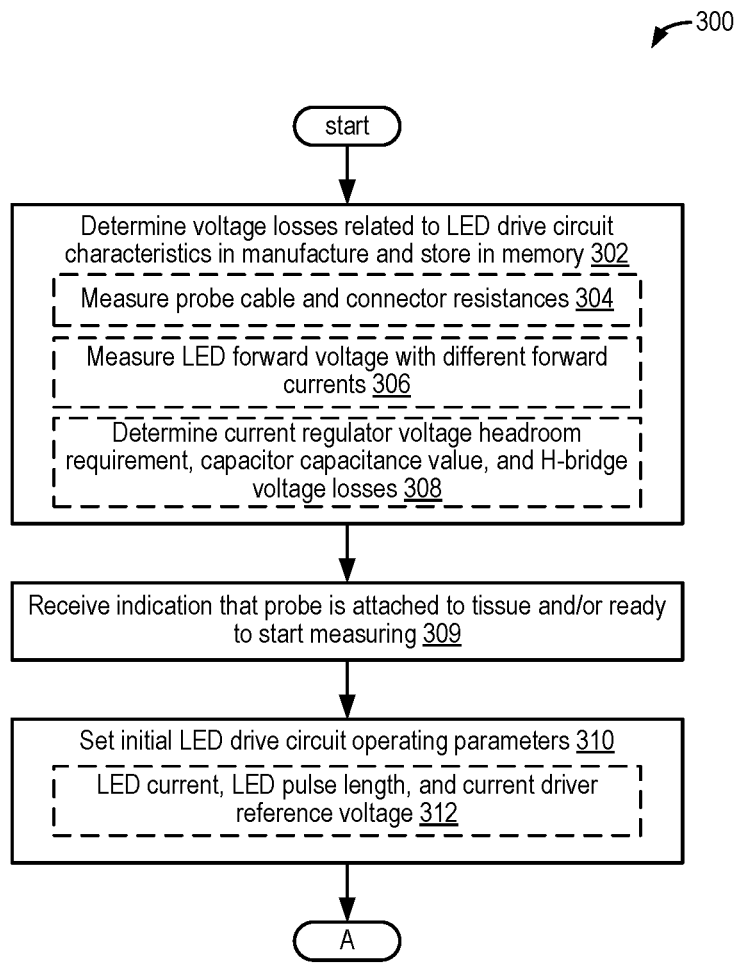
FIGS. 3A and 3B are a flow chart illustrating an example method for reducing LED drive voltage.
Figure 3B:
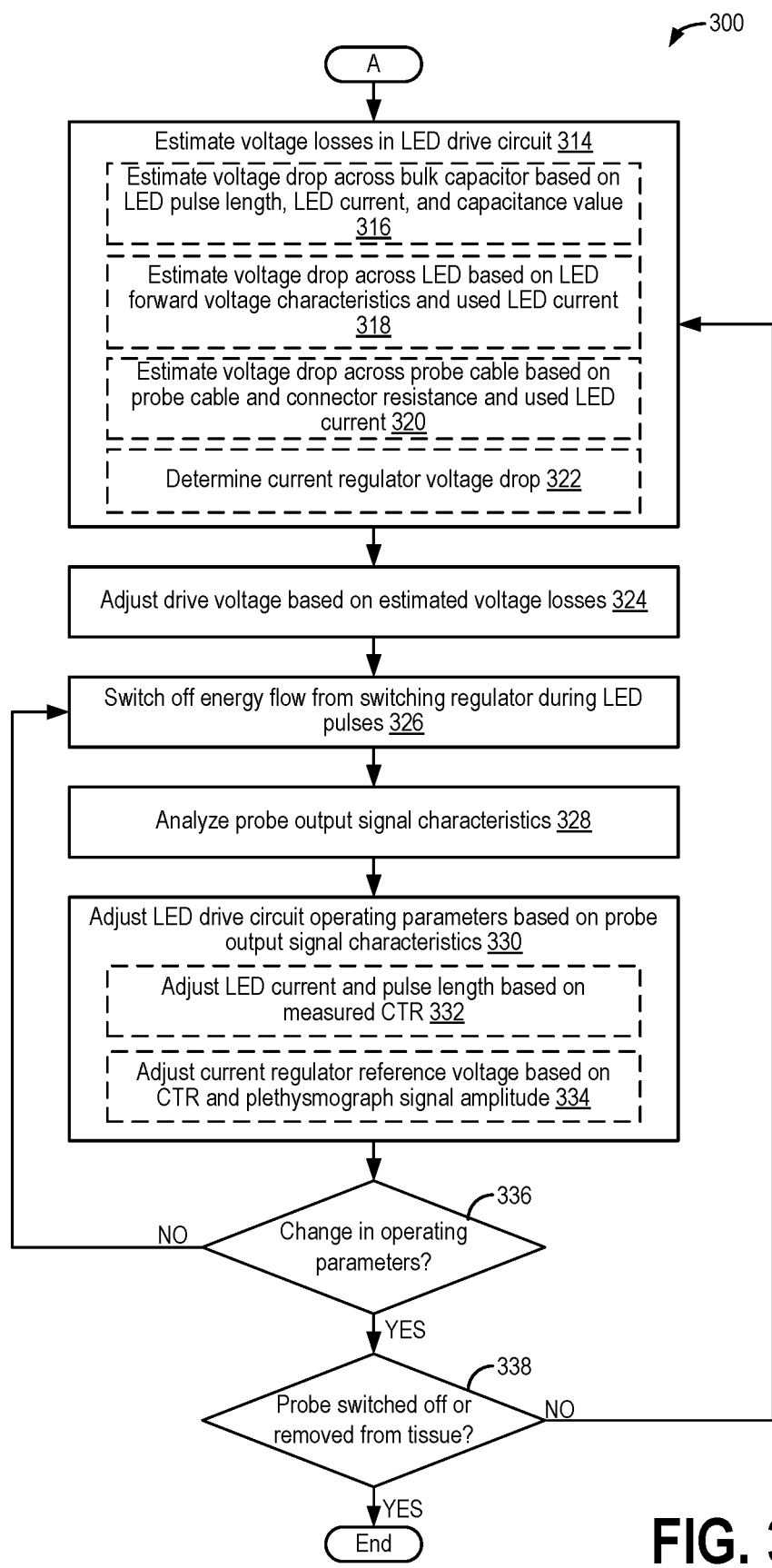

FIG. 2 schematically shows an example of LED drive and detector circuits 200, which may be included as part of pulse oximetry system 10 of FIG. 1. LED drive and detector circuits 200 includes two light emitters, herein in the form of a first light emitting diode (LED) 202 and second LED 204. When supplied with current at or above a threshold level, first LED 202 emits light of a given wavelength range, such as a range between 620 and 690 nm for red light. Second LED emits light in different range, such as in a range between 860 nm and 950 nm for infrared light. Battery 206 may be selectively couplable to the drive circuit to provide a drive voltage for illuminating the LEDs. As shown, battery 206 is coupled to a voltage regulator. The voltage regulator may be a two-channel switching regulator. For example, the voltage regulator includes a first channel (voltage regulator CH1 208) and a second channel (voltage regulator CH2 210). Voltage regulator CH1 208 and voltage regulator CH2 210 may be controlled according to signals received from timing unit 222 (included as part of an analog front end (AFE) 230).

The circuit between voltage regulator CH1 and first LED 202 includes a first bulk capacitor 212. Likewise, the circuit between voltage regulator CH2 and second LED 204 includes a second bulk capacitor 214. Each of the bulk capacitors may be charged when the respective voltage regulator channel is turned on. When a respective LED is commanded on (e.g., commanded to illuminate), current may be supplied to the LED from the bulk capacitor and the respective voltage regulator channel may be turned off. In some examples, the switching voltage regulator may be a buck-boost type regulator, and regulator switching may be turned off during a LED pulse to reduce interference coupling from the switching regulator to the LED current.

Pulse control of the LEDs may be provided by an LED control unit 216, which may be part of the AFE 230. LED control unit 216 may include a voltage controller 218 and a current regulator 220. For example, voltage controller 218 may include an input to receive pulse width modulation (PWM) data representative of what times during a corresponding PWM cycle (or other duration) LED 202 and LED 204 are to be activated. Voltage controller 218 may further include additional inputs to receive LED current (e.g., from current regulator 220) and a voltage headroom measurement. The LED control 216 may be configured to control the switching and voltage level of the voltage regulators.

Voltage controller 218 may additionally receive manufacturing data indicative of certain parameters of the drive circuit/pulse oximeter determined during manufacture (such as the forward voltage of each LED, any cable or connector resistances, etc.). The voltage headroom measurement may include the voltage over the current regulator. Voltage controller 218 may adjust the output voltage based on the manufacturing data, voltage headroom, LED current, and/or other factors, as described in more detail below.

Timing unit 222 may output a stop signal to turn off the switching voltage regulator of CH1 208 and CH2 210 during LED pulses (e.g., when LED 202 or LED 204 is illuminated). Timing unit 222 may also send a signal to current regulator 220 to activate/deactivate LED 202 or LED 204. Current regulator 220 is configured to maintain the current I1 flowing through LED 202 at or near a desired current (e.g., 100 mA) when active and maintain the current I2 flowing through LED 204 at or near a desired current (e.g., 100 mA) when active. The current flowing through each LED may be adjusted based on tissue attenuation or other parameters, and may be in a range of 10-200 mA.

AFE 230 may include further components, including an analog to digital converter 224, high-frequency and/or low-frequency oscillators, and input/output ports to communicate with the voltage regulator and with a memory (e.g., memory 112). AFE 230 further includes a detector circuit that includes a receive channel 226 and a photo detector 228. Photo detector 228 is anon-limiting example of photo detector 104 and/or 105. Photo detector 228 may detect light that is emitted from LED 202 and/or 204 (and that passes through intervening tissue) and send signals indicative of the received light to receive channel 226.

Turning now to FIGS. 3A and 3B, a flow chart illustrating a method 300 for reducing power consumption in a pulse oximeter is shown. Method 300 and the other methods described herein may be performed with a pulse oximetry system, such as pulse oximetry system 10 shown in FIG. 1. More specifically, method 300 may be executed by a control unit of the pulse oximetry system (such as control unit 110 shown in FIG. 1) according to instructions stored on a non-transitory memory of the system (e.g., memory 112 shown in FIG. 1) in combination with the various signals received at the control unit from the system components and actuation signals sent from the control unit to the emitter drive unit, input amplifier unit, etc.

Method 300 begins at 302 and includes determining voltage losses related to LED drive circuit characteristics during manufacture and storing the losses in memory. The LED drive circuit may include various components for illuminating one or more LEDs, such the components of LED drive and detector circuits 200 described with respect to FIG. 2. Therefore, separate voltage losses may be determined for individual components/subsets of components and added together to determine a total voltage drop. Determining the voltage losses related to the characteristics of the LED drive circuit includes determining cable losses by measuring probe cable and connector resistances, as indicated at 304. For example, the probe cable (e.g., cable 107 of FIG. 1) and connector resistances may be measured using an ohmmeter. Determining the voltage losses related to the characteristics of the LED drive circuit includes measuring a voltage drop (forward voltage) over each LED with one or more different forward currents, as indicated at 306. LED forward voltage depends on, e.g., a wavelength of the LED, materials that comprise the LED, LED internal and bonding resistances, and used forward current. LED forward voltage has large unit to unit variance. Forward voltage of each individual LED may be measured in probe manufacturing and written to permanent memory. Determining the voltage losses related to the LED drive circuit characteristics further includes estimating or determining remaining losses. For example, as indicated at 308, bulk capacitor capacitance (e.g., of capacitor 212 and/or 214) may be measured and written to permanent memory. Further, current regulator voltage losses and a possible H-bridge voltage drop may be determined.

At 309, method 300 optionally includes receiving an indication that the probe is attached to tissue and/or ready to start measuring. The indication may include the probe being powered on and/or an operator entering an input commanding the probe to commence measurement. After the probe is applied to the measurement site, method 300 includes setting initial LED drive circuit operating parameters at 310. The initial LED drive circuit operating parameters may include LED current, LED pulse length, LED pulse frequency, and current driver reference voltage, as indicated at 312, or other suitable parameters.

At 314, method 300 includes estimating voltage losses in the LED drive circuit based on the used LED drive circuit operating parameters and LED drive circuit characteristics. Because the determined voltage losses are specific to each LED in a single pulse oximeter probe, the initial drive voltage may be different for each LED in the probe. As a non-limiting example, the initial drive voltage may be 3.6 V for the red LED and 3.0 V for the IR LED. Furthermore, because determined voltage losses may vary from probe to probe, the initial drive voltage may also be different from unit to unit. The initial LED drive operating parameters along with the determined LED drive characteristics may be stored in memory 112 of the control unit 110. Alternatively, probe related characteristics also may be stored in a memory located in the probe.

Estimating the voltage losses during probe use may include calculating a voltage loss of the bulk capacitor based on LED pulse length, LED current, and capacitance, as indicated at 316. The LED pulse length and LED current are known to and controlled by the LED control unit, including a current regulator (e.g., current regulator 220 of FIG. 2). The capacitance is a property of the capacitor, which may be determined during manufacture and stored in memory. The pulse oximeter control unit may input the LED pulse length, the LED current, and the capacitance into one or more look-up tables, maps, or functions and output the voltage loss of the bulk capacitor, for example.

Estimating the voltage losses may include estimating a voltage drop across the LED based on LED forward voltage data measured with different LED currents in manufacturing and used LED current, as indicated at 318. The voltage drop may be interpolated based on the forward voltage values measured in manufacturing.

Estimating the voltage losses during probe use may further include determining probe cable and connector related voltage loss, as indicated at 320, for example using resistances measured in manufacturing, or the probe cable and connector resistances may be monitored while the pulse oximeter probe is connected, such as based on the voltage across the cable and the current through the cable (e.g., according to Ohm's law). Voltage across the current regulator may also be measured to ensure it is higher than the current regulator voltage headroom specification determined in the manufacturing.

Estimating the voltage losses during probe use may further include determining current regulator voltage loss, as indicated at 322. The current regulator voltage loss is dependent on the current regulator reference voltage. The current regulator reference voltage may be adjusted dynamically based on a required LED drive target SNR and a required LED current dynamic range. A higher reference voltage provides a higher SNR and a higher LED drive current. The LED drive target SNR may be set based on a perfusion of tissue being measured by the pulse oximeter probe. For example, when the perfusion (e.g., % modulation) is higher than a threshold, the target SNR may be reduced. The threshold may correspond to a perfusion value above which higher SNRs will not result in more accurate perfusion measurements. A maximum required LED current can be determined based on, e.g., the system SNR target and tissue attenuation. When the LED drive target SNR or the current driver maximum LED current is decreased, the current regulator reference voltage and the LED drive voltage can be decreased accordingly.

At 324, method 300 includes adjusting the drive voltage based on the estimated voltage losses, such as the voltage losses dynamically determined at 314. To adjust the drive voltage, the output voltage from the respective voltage regulator may be adjusted. For example, the switching frequency of the voltage regulator may be adjusted. As an example, a switching voltage regulator of each LED (e.g., voltage regulator CH1 208 and voltage regulator CH2 210 of FIG. 2) receiving voltage from a battery (e.g., battery 206 of FIG. 2) may be adjusted to reach the target drive voltage. By driving the LED circuit with the adjusted drive voltage, which is greater than the estimated voltage losses, any unit to unit or patient to patient variations will not affect LED operability.

At 326, method 300 includes turning off the energy flow from the switching regulator during LED pulses. Each LED is commanded on to emit light according to a PWM cycle (e.g., as commanded by an LED control unit, such as LED control unit 216 of FIG. 2). During each LED pulse, a stop command signal is simultaneously provided from the timing unit to the respective voltage regulator channel such that the switching regulator is turned off. Upon completion of the LED pulse, the voltage regulator may be turned on, such as described above at 324. Therefore, the voltage regulator may be switched between the LED pulses but not during the LED pulses (e.g., the voltage regulator may be effectively off during the LED pulses).

At 328, method 300 includes analyzing probe output signal characteristics, such as a current transfer ratio (CTR) and a plethysmograph signal amplitude. Based on the characteristics of the probe output signal, the LED drive circuit operating parameters may be adjusted to maintain a high SNR plethysmograph measurement, as indicated at 330. Adjusting the LED drive circuit operating parameters may include adjusting the LED current and pulse length based on the measured CTR, as indicated at 332. Additionally or alternatively, adjusting the LED drive circuit operating parameters may include adjusting the current regulator reference voltage based on the CTR and the plethysmograph signal amplitude, as indicated at 334.

At 336, method 300 includes determining if any LED drive operating parameters have changed. For example, as described above, the LED current and pulse length and/or current regulator reference voltage may be adjusted based on the CTR. If the LED drive operating parameters have changed, method 300 proceeds to 338 to determine if the change in operating parameters includes the probe being switched off and/or removed from the tissue site. If yes, method 300 ends. If the probe is still operating, method 300 goes back to 314 to estimate voltage losses based on the updated LED drive operating parameters and then again adjusts the drive voltage according to the estimated voltage losses. If at 336 no change in operating parameters are detected, for example, if no adjustments to the LED current and pulse length and/or the current regulator reference voltage were made, method 300 loops back to 326 to continue switching off the energy flow from the switching regulator during the LED pulses, analyze the probe output characteristics, and adjust the LED drive circuit operating parameters based on the probe output signal characteristics.

In this way, an LED drive voltage may be minimized based on data determined during probe manufacture and further based on operating parameters and measurements obtained during pulse oximeter probe use. The LED drive voltage may be optimized for each LED of the probe such that the drive voltage of each LED is minimized. In this way, LED power consumption may be reduced, resulting in longer probe battery life and/or smaller battery size.

Figure 4:
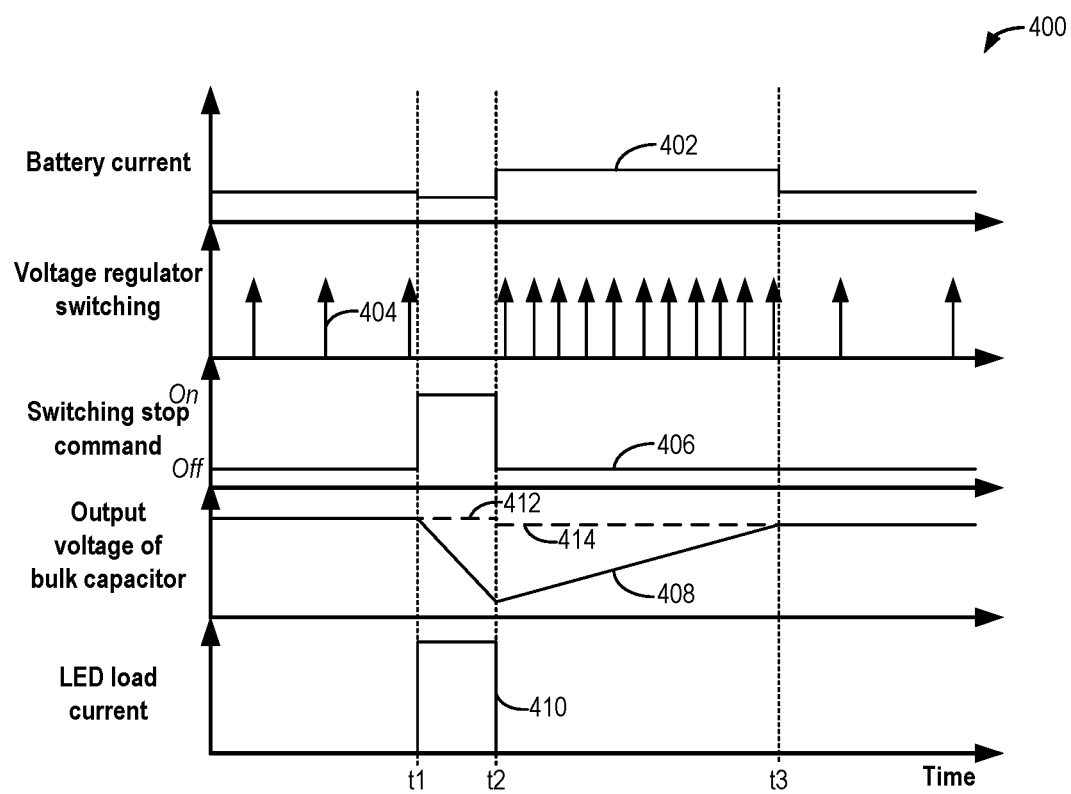
FIG. 4 is a timing diagram illustrating example drive parameters for a pulse oximetry system.

Next, FIG. 4 shows an example timeline 400 of drive parameters of an LED drive circuit of a pulse oximeter during operation, such as LED drive and detector circuit 200 of FIG. 2. Although timeline 400 shows operation of one LED drive circuit, it should be understood that a second LED drive circuit may be operated similarly, simultaneously or in sequence. Battery current is shown in plot 402, voltage regulator switching is shown in plot 404, a switching stop command is shown in plot 406, an output voltage of a bulk capacitor is shown in plot 408, and an LED load current is shown in plot 410. For all of the above, the horizontal axis represents time, with time increasing along the horizontal axis from left to right. The vertical axis represents each labeled parameter. For plots 402, 408, and 410, the value of the labeled parameter increases along the vertical axis from bottom to top. For plot 404, each arrow represents a switching event. The frequency of the switching event is high when capacitor voltage is charged (408) to the target value (412) and low when capacitor voltage is maintained at the target value. For plot 406, the vertical axis represents whether the switching stop command is "on" or "off," as labeled.

Prior to time t1, the LED (e.g., first LED 202 of FIG. 2) is off, and thus, the LED load current is zero (plot 410) and the switching stop command is off (plot 406). For example, the LED may be operated at a 5% duty cycle, and thus, the LED load current may be equal to zero for a majority of an on-and-off cycle. While the LED is off, the voltage regulator (e.g., voltage regulator CH1 208 of FIG. 2) undergoes periodic switching (plot 404) in order to maintain the output voltage of the bulk capacitor (e.g., first bulk capacitor 212 of FIG. 2) at a first target voltage indicated by dashed line 412. The first target voltage serves as a first drive voltage of the LED drive circuit. As described with respect to method 300 of FIGS. 3A and 3B and the system of FIG. 2, the switching frequency of the voltage regulator may be controlled by a timing unit (e.g., timing unit 222 of FIG. 2). With the voltage regulator turned on to provide current to the bulk capacitor, the battery current (e.g., a current of battery 206 of FIG. 2) is at a non-zero value. Note that the battery may supply current to additional pulse oximeter components in addition to the LED drive circuit of FIG. 4.

Between time t1 and time t2, the LED is switched on, with the LED load current increasing for a load pulse (plot 410). As an example, the load pulse may be 100 mA, and the pulse duration (e.g., a duration between time t1 and time t2) may be 150 μs. A timing of the load pulse is controlled by the timing unit. Simultaneously to the load pulse, beginning at time t1 and ending at time t2, the timing unit turns on the switching stop command (plot 406) such that the voltage regulator does not undergo switching (plot 404) between time t1 and time t2. While the voltage regulator is off and does not supply current to the bulk capacitor, the battery current decreases (plot 402). Furthermore, the output voltage of the bulk capacitor decreases (plot 408) as the bulk capacitor supplies current to the LED during the commanded load pulse.

Upon completion of the load pulse at time t2, the LED load current returns to zero (plot 410) and the switching stop command is turned off (plot 406). With the switching stop command turned off, the voltage regulator undergoes switching (plot 404) to charge the bulk capacitor. The frequency of switching during the charging is greater than prior to time t1, when the switching was used to maintain the output voltage at the first target voltage (dashed line 412), and the output voltage of the bulk capacitor (plot 408) increases as it is charged. Due to the more frequent switching between time t2 and time t3, the battery current increases (plot 402). Furthermore, based on determined voltage losses while operating the LED, a controller of the pulse oximeter may determine an updated, second target output voltage (dashed line 414), serving as an updated drive voltage of the LED drive circuit. Once the output voltage of the bulk capacitor (plot 408) reaches the second target output voltage (dashed line 414), the frequency of the voltage regulator switching (plot 404) decreases in order to maintain the voltage output of the bulk capacitor at the second target output voltage.

In this way, by optimizing the drive voltage in a dynamic manner, pulse oximeter LED drive power consumption may be reduced, thereby extending battery life and enabling the configuration of the pulse oximeter as a remote sensor. The configuration of the pulse oximeter as a remote probe enables continuous patient monitoring with fewer restrictions on patient movement and location. Furthermore, by extending pulse oximeter probe battery life, demands on healthcare staff may be reduced.

The technical effect of dynamically optimizing a drive voltage of an LED circuit based on measured voltage losses is that LED circuit power consumption is minimized.

An example provides a method for an optical probe including a light emitting diode (LED) in an LED drive circuit, the method including reducing power consumption of the LED drive circuit by adjusting drive voltage of the LED drive circuit based on one or more LED drive circuit characteristics and one or more LED drive circuit operating parameters. In a first example of the method, adjusting a drive voltage of the LED drive circuit comprises adjusting a voltage regulator of the LED drive circuit to supply an adjusted output voltage. In a second example of the method, which optionally includes the first example, the voltage regulator is a switching voltage regulator, and the method further includes turning off or de-coupling the switching voltage regulator during each transmission pulse of the LED. In a third example of the method, which optionally includes one or both of the first and second examples, one or more of the one or more LED drive circuit characteristics are determined during manufacture of the probe. In a fourth example of the method, which optionally includes one or more or each of the first through third examples, the one or more LED drive circuit characteristics determined during manufacture of the probe comprise one or more of measured probe cable resistance, measured probe connector resistance, and a voltage drop across the LED with different forward currents. In a fifth example of the method, which optionally includes one or more or each of the first through fourth examples, the one or more LED drive characteristics comprise a voltage drop across the LED with different forward currents, and the one or more LED drive circuit operating parameters comprise used LED current. In a sixth example of the method, which optionally includes one or more or each of the first through fifth examples, the one or more LED drive circuit characteristics comprise a capacitance of a bulk capacitor of the LED drive circuit, and the one or more LED drive circuit operating parameters comprise LED pulse length and LED current.

Another example provides a method for an optical probe including a light emitting diode (LED) driven by a drive circuit including a voltage regulator and a LED current regulator, the method including setting an LED current regulator reference voltage to an initial value; with the LED current regulator reference voltage at the initial value, measuring probe output signal characteristics; adjusting the LED current regulator reference voltage based on the probe output signal characteristics; and adjusting the LED drive voltage according to the LED current regulator reference voltage. In a first example of the method, the probe output signal characteristics comprise one or more of a plethysmograph signal amplitude and signal attenuation. In a second example of the method, which optionally includes the first example, the method further includes adjusting the LED drive voltage based on one or more LED drive circuit characteristics determined during manufacture of the probe. In a third example of the method, which optionally includes one or both of the first and second examples, the one or more LED drive circuit characteristics determined during manufacture of the probe comprise one or more of a measured probe cable resistance, a measured probe connector resistance, and a voltage drop across the LED with different forward currents. In a fourth example of the method, which optionally includes one or more or each of the first through third examples, the method further includes adjusting the LED drive voltage based on one or more of LED current and pulse length. In a fifth example of the method, which optionally includes one or more or each of the first through fourth examples, setting the LED current regulator reference voltage to the initial value comprises setting the LED current regulator reference voltage to an initial value determined during manufacture of the probe.

Another example provides for a system for an optical probe, including a light emitter; a light detector configured to measure transmission and/or reflectance of light emitted by the light emitter through blood of a patient and output a light signal to a control unit; and a drive circuit configured to control the light emitter, the drive circuit comprising: a switching voltage regulator; a bulk capacitor coupled to the switching voltage regulator and to the light emitter; and a control unit configured turn off or decouple the switching voltage regulator during each light transmission pulse of the light emitter and turn on the switching voltage regulator during inter-pulse periods to charge the bulk capacitor. In a first example of the system, the control unit processes the light signal to calculate one or more physiological parameters of the patient. In a second example of the system, which optionally includes the first example, the control unit is configured to adjust an output voltage of the switching voltage regulator based on one or more voltage losses of the LED drive circuit. In a third example of the system, which optionally includes one or both of the first and second examples, the one or more voltage losses of the LED drive circuit comprise one or more of a voltage drop across the bulk capacitor, a voltage drop across the light emitter, a cable resistance, a connector resistance, and an LED drive current regulator voltage loss. In a fourth example of the system, which optionally includes one or more or each of the first through third examples, the control unit is configured to dynamically update one or more of the voltage drop across the bulk capacitor, the cable resistance, the connector resistance, and the LED drive current regulator voltage loss when the light emitter is activated and the light detector is measuring the transmission and/or reflectance of the light emitted by the light emitter.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc., are used merely as labels and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims and may include other examples that occur to those of ordinary skill in the art. Such other examples are intended to be within the scope of the claims if they have structural elements that do not differ from the literal language of the claims or if they include equivalent structural elements with insubstantial differences from the literal languages of the claims.

The invention claimed is:

1. A method for an optical probe including a light emitting diode (LED) driven by a drive circuit including an LED drive voltage regulator and an LED current regulator, the method comprising:
   with an LED drive voltage and at least one LED drive circuit operating parameter at initial values, measuring probe output signal characteristics;
   adjusting the at least one LED drive circuit operating parameter based on the probe output signal characteristics;
   estimating LED drive circuit voltage losses based on the at least one LED drive circuit operating parameter; and
   adjusting the LED drive voltage according to the LED drive circuit voltage losses.

2. The method of claim 1, wherein the at least one LED drive circuit operating parameter is one or more of an LED current, an LED pulse length, an LED pulse frequency, and a current regulator reference voltage.

3. The method of claim 2, further comprising further adjusting the at least one LED drive circuit operating parameter in response to a change in one or more of the drive circuit operating parameters.

4. The method of claim 1, wherein probe output signal characteristics comprise one or more of a plethysmograph signal amplitude and signal attenuation.

5. The method of claim 1 wherein the LED has a plurality of transmission pulses.

6. The method of claim 1, wherein the method is carried out during continuous patient monitoring.

7. A method for an optical probe including a light emitting diode (LED) driven by a drive circuit including an LED drive voltage regulator and an LED current regulator, the method comprising:
setting initial values of the drive circuit including at least one LED drive circuit operating parameter and an LED drive voltage;
with the LED drive voltage and the at least one LED drive circuit operating parameter at the initial values, measuring probe output signal characteristics;
adjusting the at least one LED drive circuit operating parameter based on the probe output signal characteristics;
estimating LED drive circuit voltage losses based on the at least one LED drive circuit operating parameter; and
adjusting the LED drive voltage according to the LED drive circuit voltage losses.

8. The method of claim 7, wherein the at least one LED drive circuit operating parameter is one or more of LED current, LED pulse length, LED pulse frequency, and current regulator reference voltage.

9. The method of claim 8, further comprising further adjusting the at least one LED drive circuit operating parameter in response to a change in one or more of the drive circuit operating parameters.

10. The method of claim 7, wherein probe output signal characteristics comprise one or more of a plethysmograph signal amplitude and a signal attenuation.

11. A system comprising:
an optical probe including:
a drive circuit including an LED drive voltage regulator and an LED current regulator;
a light emitting diode (LED) driven by the drive circuit; and
a control unit having instructions stored in memory and configured to:
set initial values of the drive circuit including of at least one LED drive circuit operating parameter and an LED drive voltage, with the LED drive voltage and the at least one LED drive circuit operating parameter at the initial values, measure probe output signal characteristics, adjust the at least one LED drive circuit operating parameter based on the probe output signal characteristics, estimate LED drive circuit voltage losses based on the at least one LED drive circuit operating parameter, and adjust the LED drive voltage according to the LED drive circuit voltage losses.

12. The system of claim 11, wherein the at least one LED drive circuit operating parameter is one or more of LED current, LED pulse length, LED pulse frequency, and current regulator reference voltage.

13. The system of claim 11, wherein the probe output signal characteristics comprise one or more of a plethysmograph signal amplitude and a signal attenuation.

14. The system of claim 13, further comprising further adjusting the at least one LED drive circuit operating parameter in response to a change in one or more of the drive circuit operating parameters.

15. The system of claim 11 wherein the probe is a pulse oximeter probe.

16. The system of claim 15 wherein the system is a multi-wavelength pulse oximetry system.

17. The system of claim 11 further comprising a display unit.

18. The system of claim 17 wherein physiological parameters obtained via the probe are displayed on the display unit.

19. The system of claim 18 wherein the control unit and memory are located remotely from the optical probe.

* * * * *